(12) United States Patent
Walter et al.

(10) Patent No.: US 9,131,991 B2
(45) Date of Patent: Sep. 15, 2015

(54) DISPENSING DEVICE FOR A DENTAL MATERIAL

(75) Inventors: Alexander Walter, Pürgen (DE); Marc Peuker, Schöndorf (DE); Andreas J. Boehm, Reichling (DE)

(73) Assignee: 3M Innovative Properties Company, St. Paul, MN (US)

( * ) Notice: Subject to any disclaimer, the term of this patent is extended or adjusted under 35 U.S.C. 154(b) by 26 days.

(21) Appl. No.: 14/003,841

(22) PCT Filed: Mar. 7, 2012

(86) PCT No.: PCT/US2012/027933
§ 371 (c)(1),
(2), (4) Date: Dec. 2, 2013

(87) PCT Pub. No.: WO2012/122195
PCT Pub. Date: Sep. 13, 2012

(65) Prior Publication Data
US 2014/0106299 A1    Apr. 17, 2014

(30) Foreign Application Priority Data

Mar. 10, 2011    (EP) .................................... 11157752

(51) Int. Cl.
*A61C 5/04*    (2006.01)
*A61C 5/06*    (2006.01)

(52) U.S. Cl.
CPC .. *A61C 5/04* (2013.01); *A61C 5/062* (2013.01)

(58) Field of Classification Search
CPC ............... B65D 2251/0015; B65D 2251/0071; B65D 2251/223; B65D 35/44; B65D 25/48; B65D 35/36; A61C 5/066; A61C 2202/01; A61C 5/04; A61C 5/062; B05C 17/00516; A61M 5/31513; B64D 47/2018; B64D 47/2075
USPC ......... 433/80, 89, 90; 604/311; 401/128, 129, 401/183, 262; 222/149, 153.06, 183, 189, 222/326, 327, 491, 495, 541, 542, 546, 562, 222/563

See application file for complete search history.

(56) References Cited

U.S. PATENT DOCUMENTS

| 3,724,077 | A | * | 4/1973 | Preston et al. ................... 433/90 |
| 4,747,501 | A | * | 5/1988 | Greaves ........................ 215/253 |
| 5,290,105 | A | * | 3/1994 | Tencati ......................... 383/203 |

(Continued)

FOREIGN PATENT DOCUMENTS

| JP | 2006-141932 | 6/2006 |
| JP | 2006141932 A * | 6/2006 |

(Continued)

OTHER PUBLICATIONS

International Search Report for International Publ. No. PCT/US2012/027933 dated Jun. 22, 2012.

*Primary Examiner* — Cris L Rodriguez
*Assistant Examiner* — Matthew Saunders (57) ABSTRACT

A dispensing device for a dental material includes a cartridge having an outlet nozzle which forms a passageway for the dental material. The dispensing device further includes a closure which is placeable on the outlet nozzle for sealing the cartridge. The closure includes a pin for extending into the passageway, and is further adapted to seal with an outer surface of the outlet nozzle. The dispensing device is further adapted such that the pin is displaceable from the passageway by dental material dispensed from the cartridge, where the displacement causes the closure to release from the outlet nozzle. The invention may provide for relatively easy operation of the dental dispensing device.

12 Claims, 5 Drawing Sheets

(56) References Cited

U.S. PATENT DOCUMENTS

2007/0016660 A1* 1/2007 Wilson .......................... 433/89
2010/0175348 A1* 7/2010 Fundingsland et al. .... 53/111 R

FOREIGN PATENT DOCUMENTS

| WO | WO 2005/016170 | 2/2005 |
| WO | WO 2008/130798 | 10/2008 |

* cited by examiner

DISPENSING DEVICE FOR A DENTAL MATERIAL

FIELD OF THE INVENTION

The invention relates to a dispensing device for a dental material, and in particular to a dispensing device comprising a closure that automatically releases from an outlet nozzle of the device in response of dispensing dental material.

BACKGROUND ART

Dental materials are often provided in devices allowing the material to be dispensed directly to a desired location, for example on a dental pad or in a patient's mouth. Such delivery devices typically have a chamber for holding the dental material, an outlet nozzle, and a piston for extruding the material from the chamber through the outlet nozzle. To prevent the dental material from altering during storage many dispensing devices typically have a closure to seal the outlet nozzle such that the dental material is encapsulated within the chamber.

A variety of delivery devices are designed for dispensation of relatively high viscosity dental materials, like for example dental filling materials. Some of those delivery devices are configured for use with an applicator providing an extrusion force that is sufficient for dispensation of high viscosity dental materials. In dentistry several types of manually operated applicators are available which provide leverage for increasing manual forces to provide sufficient forces for extruding the dental material from the delivery device. Many applicators are designed as a reusable tool which forms part of a dental practice's basic equipment.

Although a variety of delivery devices are available there is a desire to provide a delivery device which is easy to use in, and which is further relatively inexpensive. Such a device desirably is suitable for storing the dental material over a relatively long time period.

SUMMARY OF THE INVENTION

The invention relates to a dispensing device for a dental material which comprises a cartridge for containing the dental material. The cartridge has an outlet nozzle forming a passageway for the dental material. The passageway preferably also forms an outlet within the outlet nozzle for the dental material. The dispensing device further comprises a closure which is placeable on the outlet nozzle for sealing the cartridge. The closure comprises a pin for extending into the passageway. The closure is further adapted to seal with an outer surface of the outlet nozzle. The dispensing device is further adapted such that the pin is displaceable from the passageway by dental material dispensed from the cartridge. The displacement of the pin further also causes the closure to release from the outlet nozzle.

Preferably the material of the pin and the dental material are different from each other, in particular the pin material may be different from the dental material when hardened. For example the closure, preferably comprising the pin, may not be formed from the same dental material as contained in the cartridge.

The invention is advantageous because it preferably enables a single handed removal of the closure from the cartridge. A dentist using the dispensing device of the invention therefore can activate the dispensing device for use with one hand only while simultaneously holding a second instrument, like for example a dental mirror, in the other hand. Further the dispensing device of the invention may allow for being kept sealed or inactivated (with the closure placed on the outlet nozzle) until shortly before use. Thus the quality of the dental material used may be maximized because exposure to environmental conditions (for example light, moisture, air) may be minimized. Further the invention may prevent the cartridge from being reclosed after dental material was dispensed. This may be advantageous for use of the dispensing device as a single dose dispensing device. Such a single dose dispensing device may comprise a quantity of dental material which is sufficient for a single application only, and preventing reclosing helps providing for an indication that a dispensing device already has been used. Therefore the invention may help avoiding the use of a used dispensing device. This may help minimizing a risk of cross-contamination between two patients because unintentional use of the same dispensing device with two patient's may be avoided.

In one embodiment the dispensing device contains the dental material. The dispensing device may contain a predetermined quantity of the dental material which is sufficient for a single application only. The dental material may in particular be a dental filling material, for example a light hardenable dental filling material. Generally the dental material maybe a hardenable material which preferably predominantly hardens by polymerization and cross-linking.

In one embodiment the outlet nozzle has a free end which comprises the outlet for the dental material. The closure may be adapted such that it can be placed over the free end into a sealing position in which the closure seals the outlet. In the sealing position the pin may extend from outside into the passageway. A displacement of the closure in a direction from the free end away from the nozzle preferably causes the closure to release from the nozzle. In such a released position the closure may not seal the outlet. However in the released position the pin may extend partially into the passageway or the pin may be located outside the passageway but may be retained by dental material protruding from the outlet and adhering with the pin. The closure may be removed from the cartridge, for example by stripping the closure off. In such a removed position the closure preferably is entirely separate from the cartridge, for example the closure may not be connected to the cartridge. The pin may fill a portion of the passageway in the sealing position. At a position where the pin is displaced out of the passageway that portion is preferably filled by the dental material and thus preferably prevents the closure from being displaced back toward the sealing position.

In a further embodiment the closure comprises a cap which forms a recess for receiving the outlet nozzle of the cartridge. The recess preferably accommodates the pin. A cap as referred to in this specification may generally be formed by a front wall from which a circumferential side wall protrudes. The side wall may form a circumferential free end. Further the front and side walls together may form the recess. The pin may protrude in the same direction as the side wall from the front wall. Thus the pin may be accommodated within the recess. In particular the side wall and the pin preferably form an annular space between, and that space may be adapted to receive the outlet nozzle. The pin and the side wall may protrude over generally the same length, for example may be generally flush with one another. This may provide for the closure to become entirely removable from the cartridge as the pin is entirely extruded out of the passageway.

In one embodiment the closure comprises two caps each forming a recess for receiving the outlet nozzle, and wherein only one of the recesses accommodates the pin. In this embodiment a first side wall may extend from one side of a middle wall and a second side wall may extend from an opposite side of a middle wall. Therefore the recesses may face away from each other. Such an embodiment may allow for releasing the closure from the cartridge by urging dental material toward the pin extending in the passageway, but further may allow reclosing of the cartridge by use of the recess without the pin. Thus the closure of this embodiment may be advantageous for use with a multi-dose dispensing device containing sufficient dental material for multiple applications. This is because the cartridge may be closed after use to preserve dental material remaining in the cartridge.

In one embodiment the recess forms an inner surface of the closure which generally corresponds to or matches with a negative shape of the outer surface of the outlet nozzle. The inner surface of the closure may be generally conical and the pin may be generally cylindrical. Therefore the inner surface of the closure and the outer surface of the outlet nozzle may fit with one another. The inner surface of the closure and the outer surface of the outlet nozzle may particularly fit and seal with one another. In contrast the pin and the passageway preferably form a loose fit with each other. In particular the pin and the cartridge may be adapted such that the pin and the passageway form a loose fit with each other. For example the pin may have a greatest pin diameter and the passageway may have a smallest passageway diameter, wherein the greatest pin diameter may be smaller than the smallest passageway diameter. Thus the pin may easily slide within the passageway upon urging dental material toward the pin.

In a further embodiment the pin has a deformable or resilient free end. For example the pin may have a first portion protruding from the front (or middle) wall and a second portion protruding from the first portion, and the second portion may be more deformable then first portion. In particular the second portion may be more compressible at least in a dimension in which the pin protrudes than the first portion. Thus a force applied on the pin in the dimension along which the pin protrudes may cause the second portion to compress more than the first portion. Such a force may be applied by a dental material urged toward the free end of the pin.

In one embodiment at least the pin is provided with non-stick properties with respect to a contact with the dental material. For example the pin may be coated with a non-stick coating. Further the closure may be made of a plastic material that has non-stick properties. For example the closure may be made of polytetrafluoroethylene.

In one embodiment the closure is made of a thermoplastic material. Further the closure may be made of rubber. In another embodiment the closure is made from a material selected from acrylonitrile-butadiene-styrene terpolymer, polyamide, polybutadine, polybutadiene terephthalate, polycarbonate, polyethylene, polyethylene terephthalate, polymethyl methacrylate, commonly called acrylic, polyoxymethylene, polypropylene, polystyrene, polyvinyl alcohol, polyvinylchloride.

In one embodiment the closure has retention means which are adapted to retain the closure on a surface. The retention means are preferably usable to retain the closure in a situation in which the closure is placed on the outlet nozzle. For example the retention means may be arranged at an outside of the closure. The retention means may comprise at least one of a suction cup, a rib, a groove, an elastomer, and an adhesive. The retention means may further comprise a plurality of one or more of the cup, the rib, and a groove. The retention means may allow a user of the dispensing device to retain the closure at a surface for releasing the closure from the outlet nozzle. The retention means may allow for supporting the closure to release from the cartridge. However the embodiment having retention means as described herein may in another embodiment have no pin according to the invention. In this case the closure may be removable by only using the retention means and without support of dispensing the dental material.

In one embodiment the closure is adapted to be grasped by a user in a situation in which the closure is placed on the outlet nozzle and enabling the user to remove the closure from the nozzle. For example the closure may be cap shaped and may have an annular collar protruding circumferentially from the side wall of the cap. The collar may allow for conveniently grasping the closure by a user.

In one embodiment the cartridge forms a chamber which contains the dental material. The chamber preferably extends into the cartridge at a generally uniform cross-section along a cartridge axis. Further the chamber preferably merges into the passageway. The passageway may extend at a generally uniform cross-section along a dispensing axis. The cartridge axis and the passageway axis may be inclined relative to each other by an inclination angle. The inclination angle may for example be between about 30 to about 60 degrees and in particular about 45 degrees. The chamber may be closed by a piston. The piston may be disposed within the chamber and is preferably movable within the chamber along the cartridge axis for dispensing the dental material. The dispensing device may therefore have a cartridge through which an overall channel formed by the chamber and the passageway extends. The channel is preferably closed by the closure at a front end of the cartridge and further closed adjacent a rear end of the cartridge by the piston. The dental material is preferably enclosed within the channel of the cartridge between the closure and the piston. A movement of the piston toward the front end of the cartridge preferably causes the dental material to advance toward the front end of the cartridge and thus preferably displaces the pin of the closure in a direction out of the passageway. Thereby the closure also releases from the outlet nozzle of the cartridge.

In one embodiment the dispensing device is adapted for coupling with an applicator for moving the piston. The coupling may for example be formed by a bulge or groove for engaging with a corresponding groove or bulge, respectively, of the applicator. The applicator is preferably manually operable, for example only manually operable and may not require other than manual energy for operation.

In a further aspect the invention relates to a method of dispensing a dental material. The method comprises the steps of:
   providing a dispensing device according to the invention;
   dispensing dental material from the cartridge and thereby displacing the pin from the passageway; and
   wherein the displacement causes the closure to release from the outlet nozzle.

The dispensing device in this method may particularly comprise a cartridge for containing the dental material. The cartridge may have an outlet nozzle forming a passageway for the dental material. The passageway preferably also forms an outlet within the outlet nozzle for the dental material. Further the dispensing device may comprise a closure which is placeable on the outlet nozzle for sealing the cartridge. The closure may comprise a pin for extending into the passageway. The closure is further adapted to seal with an outer surface of the outlet nozzle.

DETAILED DESCRIPTION OF THE INVENTION

Figures 1, 2:
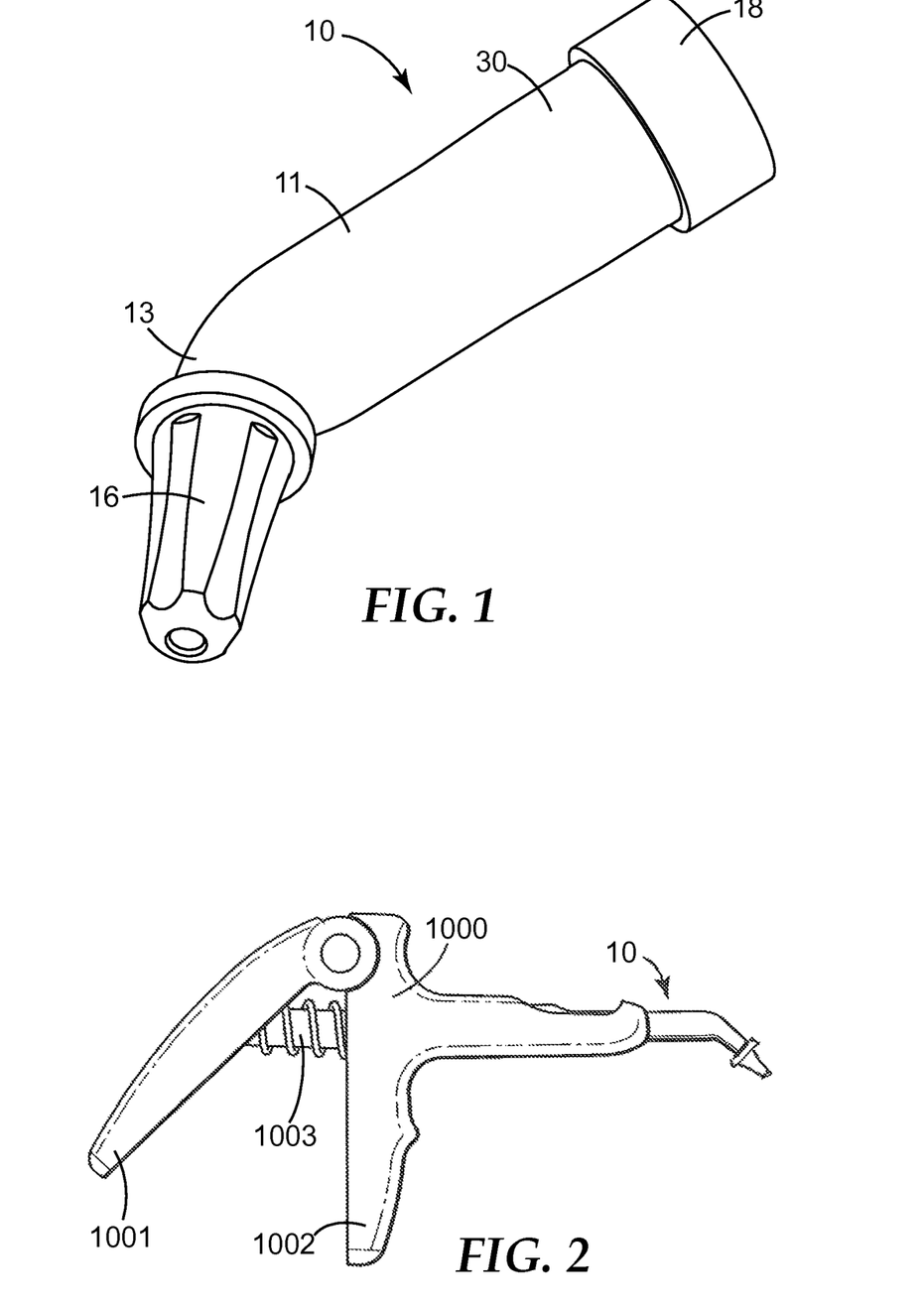
FIG. 1 is a perspective view of a dispensing device according to an embodiment of the invention.
FIG. 2 is a side view of the dispensing device shown in FIG. 1 in combination with an applicator for operation of the dispensing device.

FIG. 1 shows a dispensing device 10 for storing and dispensing a dental material according to the invention. The dispensing device 10 comprises a cartridge 11 and a closure 16. In the example the cartridge 11 is shown at a stage in which the dental material is sealed within the cartridge. Thus the dental material may be stored within the dispensing device over a relatively long period of time, for example several days, months or years. The cartridge 11 has an outlet nozzle 13 and a body 30. The outlet nozzle 13 and the body 30 may, as illustrated, merge into one another. The outlet nozzle 13 forms an outlet opening (not visible in this view) for the dental material. The outlet nozzle 13 preferably is configured to allow the dental material to be precisely dispensed to a desired location, for example in a patient's tooth. In particular the outlet nozzle 13 may protrude from the body 30 and form a free end, wherein the outlet nozzle 13 preferably tapers toward the free end. In the example the closure 16 is placed over (or accommodates) the free end of the outlet nozzle 13. Thus the closure 16 seals the outlet opening for the dental material and therefore also seals the dental material within the cartridge 11.

The cartridge further has a coupling 18 for coupling the dispensing system with an applicator device which allows application of a force to the dispensing device for extruding the dental material from the cartridge 11. The coupling 18 in the example is formed by an annular bulge around the cartridge 11, but may be formed by other means that are suitable to secure the dispensing system in an applicator. The coupling 18 is adapted for engaging with a recess of the applicator device. Such an applicator device preferably allows the dental material to be extruded from the dispensing device 10 at relatively high forces, although the manual forces applied to the applicator may be comparably low. The dispensing device 10 as shown may therefore be used for manually dispensing a high viscosity dental material, like for example a light hardenable filling material.

FIG. 2 shows a manual applicator device 1000 in combination with the dispensing device 10. The applicator device 1000 has lever 1001 and a grip 1002 which can be urged toward one another to move a plunger 1003 against the dispensing device 10. The plunger 1003 is adapted to advance a piston of the dispensing device as it is urged toward the dispensing device. The applicator device 1000 allows for leveraging a manual force applied to the grip 1002 and the lever 1001 such that the force at which the plunger 1003 is advanced is higher than the manual force applied. Therefore the applicator 1000 enables dispensing of a relatively high viscosity dental material at an acceptable manual force.

Figure 3:
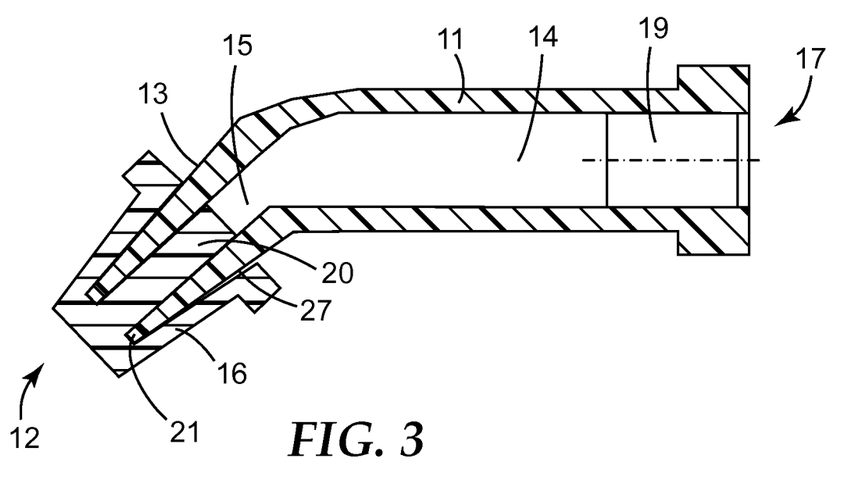
FIG. 3 is a cross-sectional view of the dispensing device shown in FIG. 1 at one stage of operation.

FIG. 3 shows the dispensing device 10 of FIG. 1 in more detail. The cartridge 11 has a front end 12 and a rear end 17. A chamber 14 for containing the dental material extends from the rear end 17 toward the front end 12 into the cartridge 11 and merges in a passageway 15 which is formed in the outlet nozzle 13 of the cartridge 11. The passageway 15 opens adjacent a front end 12 of the cartridge 11 and thereby forms the outlet opening for the dental material within the outlet nozzle 13. The chamber 14 is closed by a piston 19 which is disposed in the chamber 14 adjacent the rear end of the cartridge 14. The piston 19 preferably seals the chamber 14 and is movable toward the front end 12 for advancing the dental material toward the outlet opening.

The closure 16 is placed on the outlet nozzle 13 of the cartridge 11 and seals on an outer surface 27 of the outlet nozzle 13. Therefore the position of the closure 16 relative to the cartridge 11 as shown corresponds to a sealing position of the closure 16 and the cartridge 11. The closure 16 has a pin 20 which in the sealing position extends into the passageway 15. Thereby the pin 20 fills a portion of the passageway 15 which is kept free of dental material. The pin 20 is configured such that it is displaceable within the passageway 15. The closure 16 may be released from the outlet nozzle 13 by displacing the pin 20 of the closure 16 (in a direction from the rear end 17 toward the front end 12 of the cartridge). The pin 20 may be adapted to loosely fit within the passageway 15. The pin 120 may for example be generally cylindrical and having a smaller diameter than the smallest inner diameter of the passageway 15 in which it is placed. Thus the closure 16 may only seal on the outer surface 27 of the outlet nozzle 13, and the pin 20 may be freely displaceable within the passageway 15 without tightly sealing the passageway 15. Therefore the force for releasing the closure may be minimized. This is for example in contrast to a cylindrical pin tightly plugging a passageway. Such a pin may require a friction between the pin and an inner surface of the passageway to be overcome to displace the pin.

In the example the closure 16 forms a cap having a recess 21 for receiving the outlet nozzle 13. The shape of the recess 21 may at least partially correspond in shape to a negative shape of an outer surface 27 of the outlet nozzle 13. Thus an inner surface of the closure formed by the recess 21 may be adapted to match with the outer surface 27 of the outlet nozzle 13. In particular the recess 21 may form a conical inner surface and the outlet nozzle 13 may form a similar conical outer surface. Such conical inner and outer surfaces in a situation where they are mated preferably form a tight seal with one another. Further the conical inner and outer surfaces may provide for self-locking with each other when mated, but may be released from each other at relatively low forces. This may provide for the closure and the cartridge to be retained relative to each other with the closure and the cartridge remaining detachable from each other upon application of a certain force. Such a conical design may be relatively easy to manufacture. This may help minimizing manufacturing costs for the making of the dispensing device.

Figure 4:
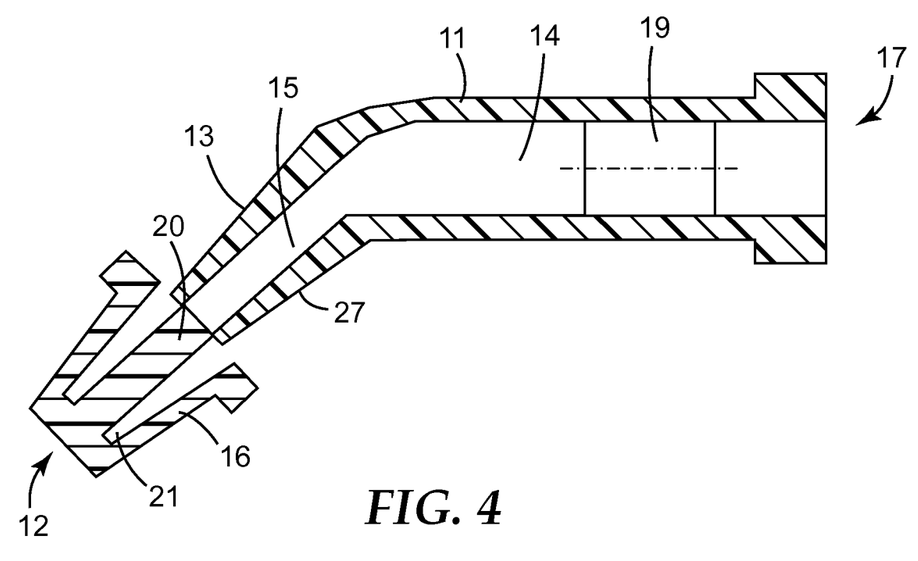
FIG. 4 is a cross-sectional view of the dispensing device shown in FIG. 1 at a further stage of operation.

FIG. 4 shows the dispensing device 10 at a stage at which the closure 16 is released from the outlet nozzle 13, but still in contact with the outlet nozzle 13. In particular at the stage shown the pin 20 of the closure 16 is displaced entirely out of the passageway 15. In the example the displacement of the pin 20 results from a displacement of the dental material advanced toward the outlet nozzle 13 by the piston 19. The closure 16 at the stage shown may be held in place due to the dental material and the pin 20 adhering with one another. Thus the closure 16 may not immediately fall off as the pin 20 exits the passageway 15. This may be advantageous for a user to remove and accommodate the closure 16 in a controlled way. The closure 16 may be finally removed from the cartridge 11 by manually shaking or stripping the closure off from the outlet nozzle 13.

In an example the dispensing device 10 may be used with an applicator device (as shown in FIG. 2) in a dental practice. A dentist may with a single hand grasp the applicator, advance some of the dental material to cause the closure 16 to release from the outlet nozzle 13, and remove the closure 16 by shaking or stripping the closure 16 off. Once the closure 16 is removed the dispensing device 10 is ready for applying the dental material, for example in a patient's mouth. Thus the dispensing device 10 allows for single handed preparation for use (including removal of the closure) and for single handed operation. This may be advantageous in particular for a dentist holding a further instrument (for example a mirror) in the other hand. Further the dispensing device may allow a dentist's assistant to prepare the dispensing device 10 for use some time before the actual use. This is because the dispensing device 10 may not require the closure 16 to be removed by the dentist's assistant already during preparation of the dispensing device 10, but enables the closure 16 to be easily removed by the dentist only shortly before use. Therefore the dispensing device 10 may—although prepared for use—be left with the closure 16 sealing the outlet nozzle 13. The dental material, which may be sensitive to environmental conditions, like air, moisture, or light, may be preserved from alteration as long as the closure 16 and the cartridge are in the sealing position. Therefore the preparation of the dispensing device 10 for use may be independent from the time it is used by the dentist. The delivery system may for example be prepared several minutes or hours prior to an actual use without the dental material getting affected.

Figure 5:
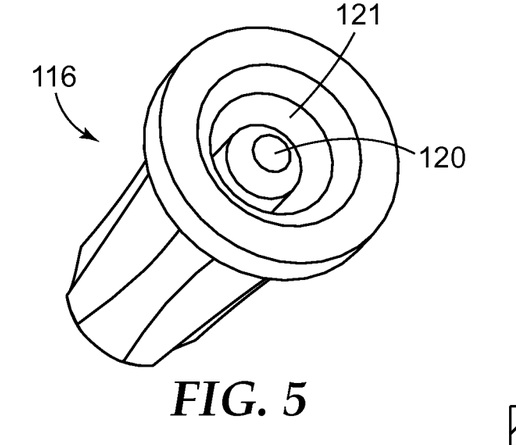
FIG. 5 is a perspective view of a closure of a dispensing device according to an embodiment of the invention.
Figure 6:
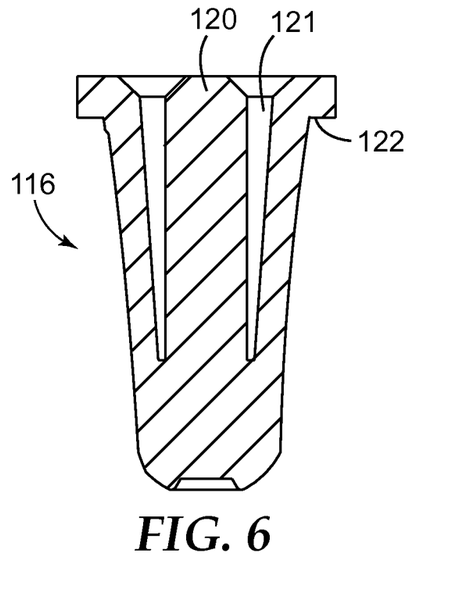
FIG. 6 is a cross-sectional view of the closure shown in FIG. 5.

FIG. 5 shows a closure 116 of a dispensing device of the invention, for example one as shown in FIG. 1. The closure 116 forms a cap which comprises a pin 120 within a recess 121 of the cap. A cross-section of the cap 116 is shown in FIG. 6. The recess 121 of the closure 116 forms a conically shaped inner surface of the closure 116. Thus the closure 116 is adapted to fit on a conically shaped outer surface of an outlet nozzle (not shown). Therefore a good seal may be achieved between the inner surface of the closure and the outer surface of the outlet nozzle. The closure 116 further has a collar 122 which may allow a user to remove the closure by just manually pulling the cap from the outlet nozzle.

Figure 7:
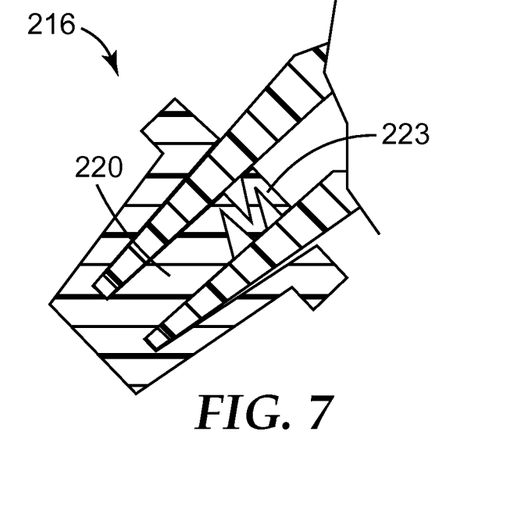
FIG. 7 is a partial cross-sectional view of a further closure of a dispensing device according to an embodiment of the invention.

FIG. 7 shows a further embodiment of a closure 216 of the invention. The closure 216 may be generally configured as a closure shown in FIGS. 5 and 6 (or another Figure of this specification), but has a pin 220 which has a deformable free end 223. In the example the deformable free end 223 is resilient, and in particular is formed by a spring. The deformable free end 223 may prevent the closure from releasing from an outlet nozzle during storage of a dispensing device. It has been found that the dental material may slightly change in volume during storage, for example may slightly expand or contract due to variations in temperature. The deformable free end 223 may compensate for the expansion and/or contraction of the dental material and therefore may prevent the closure from unintentional releasing.

Figure 8:
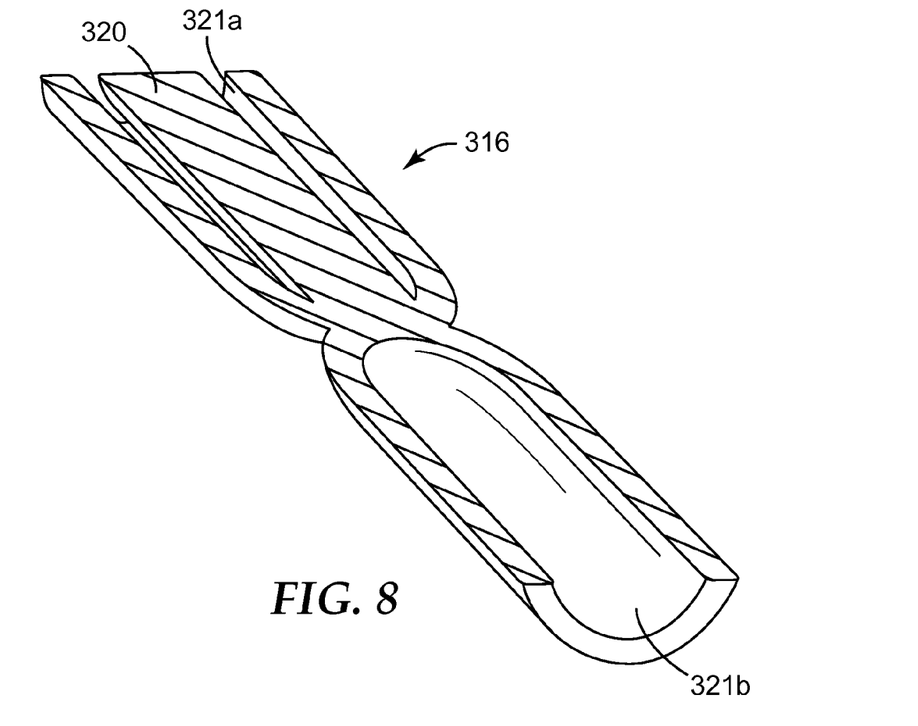
FIG. 8 is a perspective cross-sectional view of another closure of a dispensing device according to an embodiment of the invention.

FIG. 8 shows another embodiment of a closure 316. The closure 316 forms a dual cap having two recesses 321a, 321b. In the example shown the recesses 321a, 321b face away from each other, but may in another example be generally arranged otherwise such that each of the recesses is usable with an outlet nozzle of a dispensing device independently from the respective other recess. A pin 320 is accommodated in only one of the recesses (321a). Therefore the closure 316 may be placed with the recess 321a—being the recess having a pin—on an outlet nozzle of the dispensing device during an initial storage (for example at a stage at which the dispensing device is still unused). Further the closure 316 may be placed with the recess 321b—being the recess having no pin—on the outlet nozzle for reclosing the dispensing device, for example after a quantity of dental material having been dispensed from the dispensing device.

Figure 9:
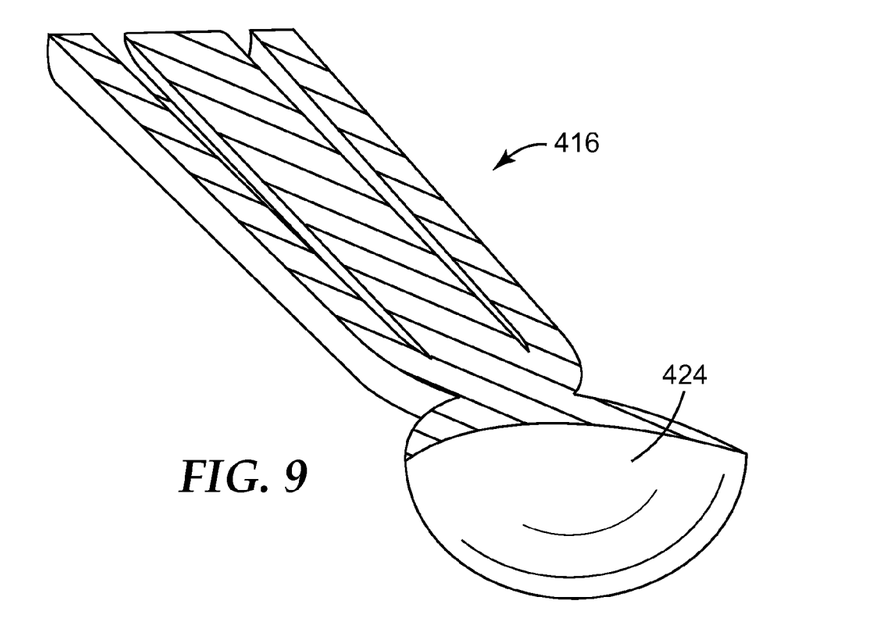
FIG. 9 is a perspective cross-sectional view of a further closure of a dispensing device according to an embodiment of the invention.

FIG. 9 shows still a further embodiment of a closure 416 of the invention. The closure 416 may be generally configured like any closure shown in another Figure of this specification, but additionally has a suction cap 424. The suction cap 424 is arranged at the closure such that it can be retained on a surface in a situation where the closure 416 is placed on an outlet nozzle of a dispensing device. Thus a user, for example a dentist, may retain the closure 416 by use of the suction cap 424 on a surface before releasing the closure from the nozzle. Thus a controlled removal and accommodation of the removed closure may be provided.

Figure 10:
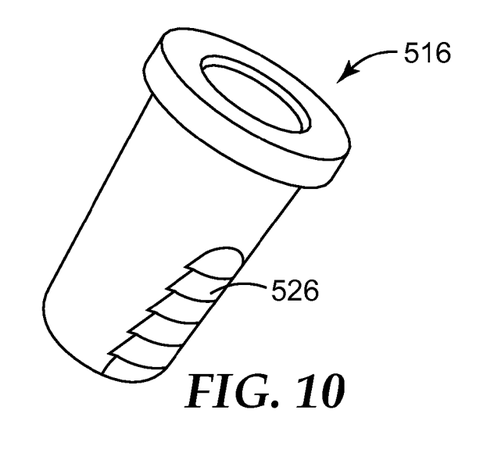
FIG. 10 is a perspective view of a further closure of a dispensing device according to an embodiment of the invention.

FIG. 10 shows a further embodiment of a closure 516. The closure 516 may be generally configured like any closure shown in another Figure of this specification, but additionally has a retention structure 526 for retaining the closure at a surface. The retention structure 526 may comprise one or more edges, barbs or hooks. Thus the closure 516, once released from a nozzle, may be entirely removed from the nozzle by retaining the closure 516 at the retention structure 526 and pulling the nozzle away from the retention structure 526. The retention structure 526 in the example is based on a generally flat face of the closure.

Figure 11:
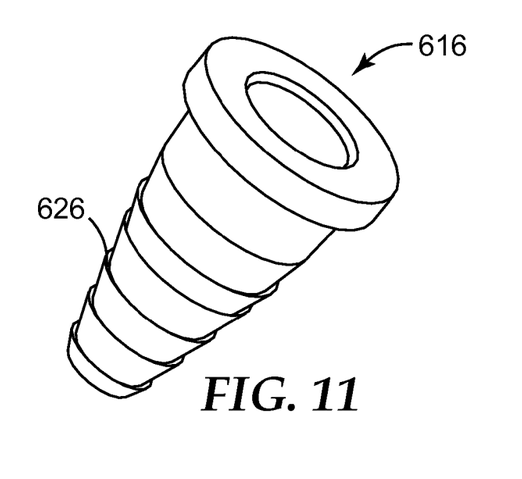
FIG. 11 is a perspective view of still a further closure of a dispensing device according to an embodiment of the invention.

In another example as shown in FIG. 11 a retention structure 626 extends circumferentially around a closure cap 616.

Figure 12:
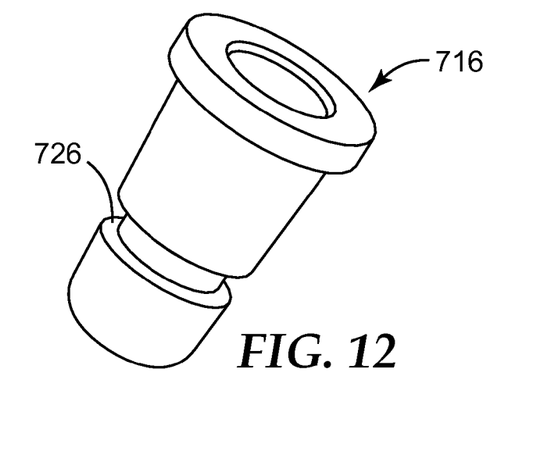
FIG. 12 is a perspective view of a closure for a dispensing device according to an embodiment of the invention.

FIG. 12 shows a further retention structure 726 in the form of a circumferentially extending groove within a closure cap 716.

The invention claimed is:

1. A dispensing device for a dental material, comprising:
a cartridge for containing the dental material, the cartridge having an outlet nozzle with an outer surface and an inner surface, the inner surface forming a passageway for the dental material; and
a closure, not being formed from the dental material, having a cap and a pin, the cap having a front wall from which a circumferential side wall extends, the circumferential side wall having an inner surface defining a conical passageway that generally corresponds to a negative shape of an outer surface of the outlet nozzle, and where the pin protrudes generally in the same direction as the side wall from the front wall over generally the same length, the closure forming a seal only between the outer surface of the cartridge and the circumferential side wall of the closure and the pin extending into the passageway of the cartridge with a loose fit to allow the closure to move relative to the outlet nozzle under pressure from the dental material dispensed from the cartridge.

2. The dispensing device of claim 1, containing the dental material.

3. The dispensing device of claim 1, wherein the closure comprises two caps each forming a recess for receiving the outlet nozzle, and wherein only one of the recesses accommodates the pin.

4. The dispensing device of claim 1, wherein the pin has a deformable or resilient free end.

5. The dispensing device of claim 1, wherein at least the pin is provided with non-stick properties with respect to a contact with the dental material.

6. The dispensing device of claim 1, wherein the closure has retention means to retain the closure on a surface, the retention means comprising at least one of a suction cup, a rib, a groove, an elastomer, and an adhesive, and wherein the retention means are usable to retain the closure in a situation in which the closure is placed on the outlet nozzle.

7. The dispensing device of claim 1, wherein the closure includes a surface that can be grasped by a user in a situation in which the closure is placed on the outlet nozzle and enabling the user to remove the closure from the nozzle.

8. The dispensing device of claim 1, wherein the cartridge forms a chamber which contains the dental material, the chamber extending at a generally uniform cross-section into the cartridge along a cartridge axis and merging into the passageway.

9. The dispensing device of claim 8, wherein the chamber is closed by a piston which is movable within the chamber along the cartridge axis for dispensing the dental material.

10. The dispensing device of claim 9 coupled with an applicator for moving the piston.

11. The dispensing device of claim 1, wherein the dental material is a dental filling material.

12. A method of dispensing a dental material, comprising the steps of:
- providing a dispensing device according to any of the preceding claims;
- dispensing dental material from the cartridge and thereby breaking the only seal between the outer surface of the cartridge and the circumferential side wall of the closure and displacing the pin from the passageway; and
- wherein the displacement causes the closure to release from the outlet nozzle.

* * * * *